017# United States Patent [19]

Ponticello

[11] Patent Number: 4,598,149

[45] Date of Patent: Jul. 1, 1986

[54] 3-AMINO-2-HYDROXYPROPYL OF PYRIMIDIN-4-ONE USEFUL AS ANTIHYPERTENSIVE, CARDIOPROTECTIVE, ANTIARRYTHMIC, AND ANTIANGINAL AGENTS

[75] Inventor: Gerald S. Ponticello, Lansdale, Pa.

[73] Assignee: Merck & Co., Inc., Rahway, N.J.

[21] Appl. No.: 585,739

[22] Filed: Mar. 2, 1984

[51] Int. Cl.$^4$ .................. C07D 239/02; C07D 403/00; A61K 31/505

[52] U.S. Cl. ................................ 544/319; 544/295; 544/296; 544/333; 544/334; 544/335; 544/357; 544/405; 546/276; 548/518; 549/59; 549/68; 549/472; 549/480

[58] Field of Search ............... 424/251; 514/274, 269, 514/255, 252; 544/319, 333, 335, 334, 295, 296

[56] References Cited

U.S. PATENT DOCUMENTS

| | | | |
|---|---|---|---|
| 3,946,009 | 3/1976 | Wasson et al. | 424/250 |
| 4,027,027 | 5/1977 | Jaeggi et al. | 544/319 |
| 4,042,586 | 8/1977 | Wasson et al. | 544/60 |
| 4,115,575 | 9/1978 | Froi et al. | 424/250 |
| 4,195,090 | 3/1980 | Froi et al. | 424/250 |
| 4,410,530 | 10/1983 | Frei et al. | 544/319 |

OTHER PUBLICATIONS

Alfred Burger, Medicinal Chem. 2nd edition, 1960, p. 42.
Antonio et al., Chem. Abst. 88:31869m.
Frei et al., Chem. Abst. 86:121372g.
Frei et al., Chem. Abst. 81:135967p.

Primary Examiner—Donald G. Daus
Assistant Examiner—Cecilia Shen
Attorney, Agent, or Firm—Alice O. Robertson; Salvatore C. Mitri; Michael C. Sudol

[57] ABSTRACT

The novel compounds of this invention and their pharmaceutically acceptable salts exhibit cardioselective $\beta$-adrenergic blocking activity, with a direct relaxing effect on the $\beta_2$-adrenergic receptors and are useful as antihypertensive, cardioprotective, antiarrhythmic and, antianginal agents.

9 Claims, No Drawings

3-AMINO-2-HYDROXYPROPYL OF PYRIMIDIN-4-ONE USEFUL AS ANTIHYPERTENSIVE, CARDIOPROTECTIVE, ANTIARRYTHMIC, AND ANTIANGINAL AGENTS

SUMMARY OF THE INVENTION

This invention is concerned with novel compounds of general structural formula, I:

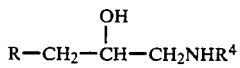

wherein R is:

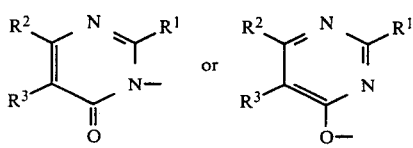

and $R^1$, $R^2$, $R^3$ and $R^4$ are as defined below.

These novel compounds and their pharmaceutically acceptable salts exhibit cardioselective β-adrenergic blocking activity, with a direct relaxing effect on the $β_2$-adrenergic receptors and are useful as antihypertensive, cardioprotective, antiarrhythmic, and antianginal agents.

BACKGROUND OF THE INVENTION

A class of pharmaceutical agents known as β-adrenergic blocking agents, are available which affect cardiac, vascular and pulmonary functions and are mild antihypertensives. Specifically, these agents have the capability of reducing heart rate, without counteracting vasodepression or suppressing bronchodilation. β-adrenergic blocking agents, their chemical structure and activity, are disclosed in *Clinical Pharmacology and Therapeutics*, 10, 292–306 (1969). Various β-adrenergic blocking agents are also described in the following patents: U.S. Pat. No. 3,048,387; U.S. Pat. No. 3,337,628; U.S. Pat. No. 3,655,663; U.S. Pat. No. 3,794,650; U.S. Pat. No. 3,832,470; U.S. Pat. No. 3,836,666; U.S. Pat. No. 3,850,945; U.S. Pat. No. 3,850,946; U.S. Pat. No. 3,850,947; U.S. Pat. No. 3,852,291; U.S. Pat. No. 4,134,983; U.S. Pat. No. 4,199,580; U.S. Pat. No. 4,115,575; U.S. Pat. No. 4,195,090; British Pat. No. 1,194,548; and South African Pat. No. 74/1070.

Now, with the present invention there are provided novel cardioselective β-blocking agents; processes for their synthesis, pharmaceutical formulations comprising one or more of the novel compounds; and methods of treatment with the novel compounds or pharmaceutical compositions thereof wherein an antihypertensive, cardioprotective, antiarrhythmic or antianginal agent is indicated.

DETAILED DESCRIPTION OF THE INVENTION

The novel compound of this invention has structural formula I:

$$R-CH_2-\underset{\underset{\text{OH}}{|}}{CH}-CH_2-NH-R^4 \quad\quad I$$

or a pharmaceutically acceptable salt thereof wherein; R is

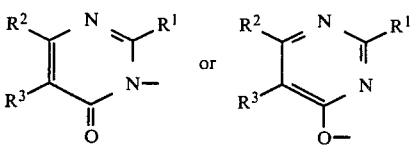

$R^1$ and $R^2$ are independently
 (1) hydrogen,
 (2) $C_{1-8}$alkyl, either straight or branched chain,
 (3) carbocyclic aryl such as phenyl or naphthyl, either unsubstituted or substituted with 1 to 3 substituents selected from:
   (a) halo, such chloro, fluoro or bromo,
   (b) $C_{1-3}$alkoxy, or
   (c) $C_{1-3}$alkyl;
 (4) heterocyclic aryl of 5 or 6 members, at least 4 of which are carbon atoms and the hetero atoms are O, N or S such as pyridinyl, pyrazinyl, pyrimidinyl, thienyl, furyl, N-methylpyrryl or the like;
$R^3$ is
 (1) hydrogen,
 (2) halo such as fluoro, chloro or bromo, preferably fluoro or chloro,
 (3) $C_{1-8}$alkyl, either straight or branched chain; and
$R^4$ is
 (1) $C_{1-8}$alkyl, either straight or branched chain,
 (2) $C_{3-6}$cycloalkyl,
 (3) aryl-$C_{1-4}$alkyl, wherein the $C_{1-4}$alkyl moiety is straight or branched chain, and the aryl moiety is phenyl or naphthyl, either unsubstituted or substituted with 1 or 2 substituents selected from $C_{1-3}$alkyl, $C_{1-3}$alkoxy, hydroxy and halo such as chloro, fluoro or bromo.

A preferred embodiment of the novel compound is that in which:
$R^1$ is
 (1) $C_{1-8}$alkyl, especially methyl, or
 (2) aryl, either unsubstituted or substituted, especially phenyl or 4-methoxyphenyl;
$R^2$ is
 (1) $C_{1-8}$alkyl, especially methyl, or
 (2) phenyl;
$R^3$ is
 (1) hydrogen,
 (2) $C_{1-8}$alkyl, especially methyl, or
 (3) halo, especially chloro; and
$R^4$ is
 (1) $C_{1-8}$alkyl, especially 2-propyl, or tert-butyl,
 (2) aryl-$C_{1-4}$alkyl, especially wherein the $C_{1-4}$alkyl moiety is ethyl or 2-propyl, and the aryl moiety is phenyl substituted with two $C_{1-3}$alkoxy groups, especially methoxy, or
 (3) $C_{3-6}$ cycloalkyl, especially cyclopropyl.

The compounds of the present invention have an asymmetric carbon in the propyl side chain and therefore are resolvable into (R)— and (S)—enantiomers. This invention includes these optical isomers and mixtures of the isomers such as racemic mixtures. The substituent $R^4$ may also include an asymmetric carbon, and all of the isomers and mixtures thereof resulting from the introduction of that second asymmetric carbon also are deemed to be within the scope of this invention.

The compounds of the present invention also include the non-toxic pharmaceutically acceptable acid addition and quaternary ammonium salts thereof. The acid addition salts are prepared by treating the compounds with an appropriate amount of a suitable organic or inorganic acid. Examples of useful organic acids are carboxylic acids such as maleic acid, tartaric acid, acetic acid, pamoic acid, oxalic acid, propionic acid, salicylic acid, succinic acid, citric acid, maleic acid, isethionic acid, or the like. Useful inorganic acids are hydrohalo acids such as hydrochloric, hydrobromic, sulfuric, phosphoric acid, or the like.

Quaternary salts are prepared by any suitable method, for example, by reacting any compound of the present invention having the tertiary amine group —NHR[1] with an alkyl halide, preferably the iodide such as ethyliodide or methyliodide, in a suitable solvent such as methanol, ethanol or dimethylformamide (DMF). The reaction is generally carried out at room temperature. The quaternary salt is obtained directly on removing the solvent.

The novel process of this invention may be depicted as follows:

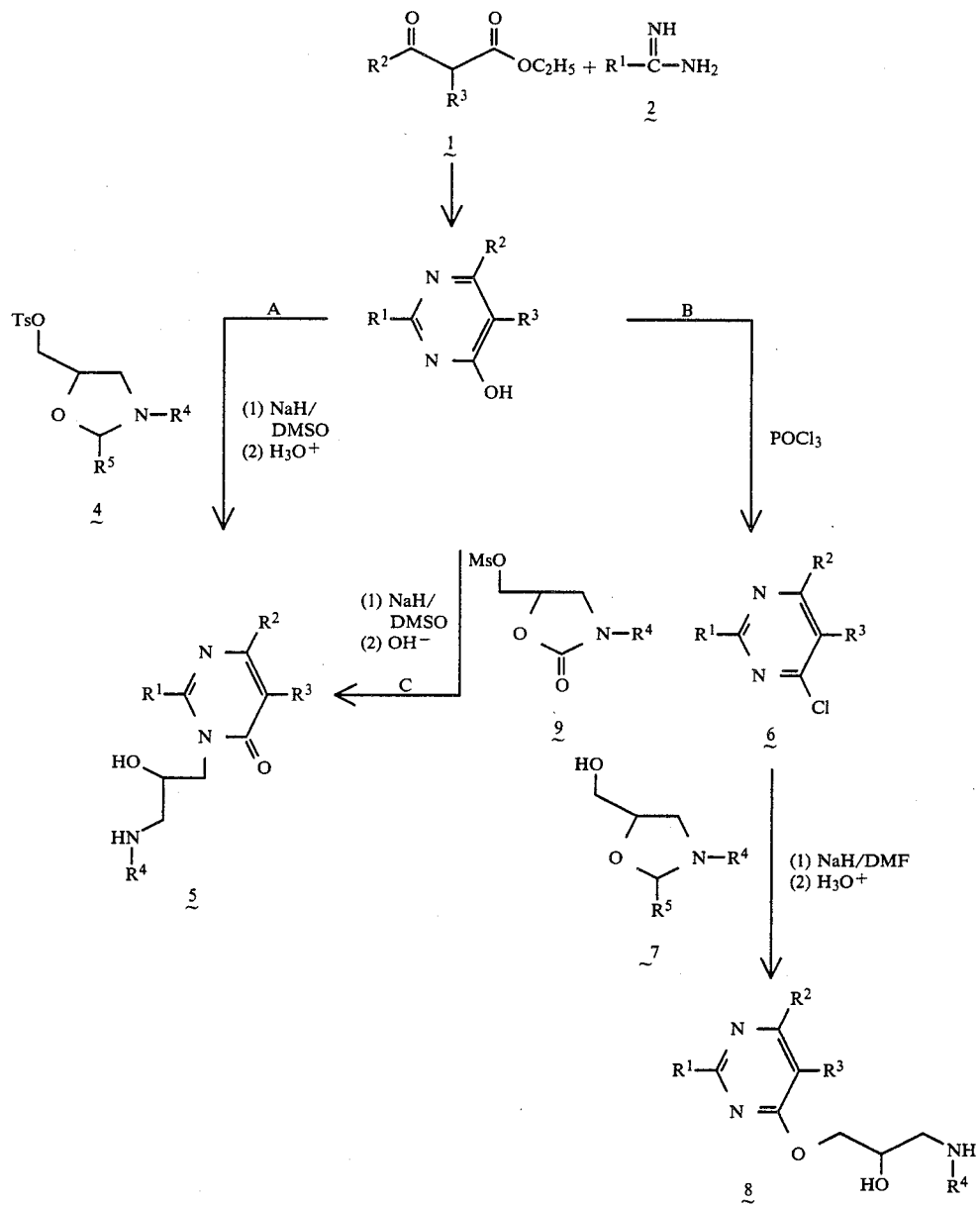

$R^5$ is aryl such as phenyl, substituted phenyl, naphthaldehyde, or the like, or $C_{1-3}$ alkyl.

The 6-hydroxypyrimidine intermediate 3 can be prepared by any of the methods known in the art, especially by those described in Elderfeld's Heterocyclic Compounds, Vol. 6. A preferred method is via the reaction of an amidine 2 with a substituted β-keto ester of type 1 as shown in the reaction scheme.

Method A:

6-Hydroxypyrimidine, 3, is reacted with the oxazolidine tosylate, 4. The tosylate group can be substituted by any other suitable leaving group such as mesylate, triflate or iodide. The reaction is conducted in the presence of a base such as NaH, NaOCH$_3$, NaOH, potassium tert-butoxide, or the like, preferably NaH in an appropriate solvent such as DMSO, DMF, toluene, methanol, water or the like, preferably DMF, at a temperature of about 0° C. to the reflux temperature of the solvent over a period of about 1 to 48 hours, preferably at about 110° C. for 18 hours to obtain an oxazolidine intermediate. The oxazolidine intermediate is then subjected to acid hydrolysis using an acid such as aqueous HCl, H$_2$SO$_4$, CH$_3$COOH, or the like, at about 0° C. to the reflux temperature of the solvent for about 15 minutes to 15 hours, preferably in 1N HCl for 15 minutes at 100° C. to obtain the 6-pyrimidinone, 5.

Method B:

In Method B, 6-hydroxypyrimidine, 3 is converted to the 6-chloropyrimidine, 6, using POCl$_3$, PCl$_5$, SOCl$_2$ or the like in a solvent such as excess reagent, benzene, toluene, THF or the like at about 0° C. to the reflux temperature of the solvent for 1 to 12 hours, preferably with POCl$_3$ at reflux for 3 hours to obtain the 6-chloropyrimidine, 6.

Reaction of 6 with the oxazolidine 7 in the presence of a suitable base such as NaH, NaOCH$_3$, potassium tert-butoxide or the like, preferably NaH, in an appropriate solvent such as DMSO, DMF, toluene, CH$_3$OH or the like, preferably DMF, at about 0° C. to the reflux temperature of the solvent over a period of about 1 to 48 hours preferably 110° C. for 18 hours provides an oxazolidine intermediate. Hydrolysis of this intermediate proceeds as described in Method A.

In Method C, the 6-hydroxypyrimidine, 3, is first reacted with base and the oxazolidinone mesylate, 8, prepared according to the methods described in Canadian Pat. No. 965,787 as tosylate, triflate or iodide preferably using NaH as base, DMSO as solvent at 60° C. for 2 hours, followed by treatment with an aqueous base such as NaOH, KOH or the like at a strength of 1–40% w/v in an appropriate solvent such as methanol, ethanol, acetone, THF, or the like (preferably 10% NaOH—C$_2$H$_5$OH, 1:1) at the reflux temperature of the solvent over a period of about 15 minutes to 24 hours, preferably for 2 hours at 100° C. to provide the 6-pyrimidine, 5.

The novel compounds of this invention are active as cardioselective β-adrenergic receptor blocking agents and hence useful as antihypertensive, cardioprotective, antiarrhythmic, and antianginal agents.

For use as antihypertensives and/or β-adrenergic blocking agents, the present compounds can be administered transdermally, orally or parenterally; i.e., intravenously, interperitoneally, etc. and in any suitable dosage form. The compounds may be offered in a form (a) for oral administration; e.g., as tablets, in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for parenteral administration; e.g., dissolved or dispersed in a suitable liquid carrier or emulsifier; or (c) as an aerosol or drug-impregnated patch for transdermal administration. Generally, doses of the novel compounds of from about 0.01 to about 50 mg/kg day/and preferably from about 0.1 to about 20 mg/kg of body weight per day are used. Dosage may be single or multiple depending on the daily total required and the unit dosage.

EXAMPLE 1

(S)-5-Chloro-N'-[3-(3,4-dimethoxyphenylethylamino)-2-hydroxypropyl]-2-(4-methoxyphenyl)-4-methyl-6-pyrimidone Hydrochloride Step A: Preparation of 5-Chloro-6-hydroxy-4-methylpyrimidine Under N$_2$, a solution of ethyl 2-chloroacetoacetate (1.8 ml, d=1.15, 0.013 mol) in CHCl$_3$ (50 ml) was added dropwise to a solution 4-methoxybenzamidine (3.9 g, 0.026 mol) in CHCl$_3$ (100 ml). After stirring overnight, the reaction mixture was filtered and the filtrate was washed with dilute NaOH solution. The aqueous layer was extracted with CH$_2$Cl$_2$ (3×) and the organic layer was dried, filtered and concentrated to dryness. The residue was chromatographed on silica gel and the product was eluted with 2% CH$_3$OH-CHCl$_3$ (v/v) to yield 0.7 g (22%) of product m.p. 250°–251° C.

Step B: Preparation of (S)-5-chloro-N'-[3-(3,4-dimethoxyphenylethylamino)-2-hydroxypropyl]-2-(4-methoxyphenyl)-4-methyl-6-pyrimidone hydrochloride Under N$_2$, a mixture of product from Step A (0.5 g, 2 mmol), NaH (60% oil dispersion, 0.09 g, 2.25 mmol) in DMSO (20 ml) was heated at 60° C. for 0.5 hours. A solution of (S)-3-(3,4-dimethoxyphenylethyl)-5-(hydroxymethyl)oxazolid-2-one mesylate (0.72 g, 2 mmol) in DMSO (20 ml) was added dropwise. After 15 hours at 60° C., the mixture was poured into water and the aqueous phase was extracted with CH$_2$Cl$_2$ (3×). The organic layers were backwashed with H$_2$O, saturated NaCl, dried, filtered and concentrated to dryness. The residue was treated with ethanol (25 ml) and 10% NaOH (25 ml) and heated at reflux. After 2 hours the reaction was cooled, poured into water and the aqueous phase was extracted with CHCl$_3$ (3×). The organic extracts were dried, filtered and concentrated to dryness. The residue was chromatographed on silica and the product was eluted with 3% CH$_3$OH—CHCl$_3$ saturated with NH$_3$. The crude product was converted to the HCl salt and crystallized from 2-propanol to yield 155 mg (16%) of final product, m.p. 126°–130° C.

Using 2,4,5-trimethylpyrimidin-6-one in place of 5-chloro-4-methyl-2-(p-methoxyphenyl)-pyrimidine-6-one as described in Example 1 yielded (S)-N'-[3-(3,4-dimethoxyphenylethyl)amino-2-hydroxypropyl]-2,4,5-trimethylpyrimidine-6-one.

EXAMPLE 2

(S)-N'-[3-(3,4-dimethoxyphenylethylamino)-2-hydroxypropyl]-2-(4-methoxyphenyl)-4-methyl-6-pyrimidone hydrochloride sesquihydrate Step A: Preparation of 6-hydroxy-4-methyl-2-p-methoxyphenylpyrimidine Under N$_2$, a solution of ethyl acetoacetate (7.15 g, 0.053 mol) in CHCl$_3$ (200 ml) was added dropwise to a suspension of 4-methoxybenzamidine in CHCl$_3$ (200 ml). After stirring at room temperature overnight, water was added to the solution. The aqueous phase was separated and extracted with CHCl$_3$ and the organic layers were combined, dried (Na$_2$SO$_4$), filtered and concentrated to dryness. The residue was chromatographed on silica gel and the product was eluted with 2% CH$_3$OH—CHCl$_3$ to yield 8.58 g (75%) of product, m.p. 198°–199° C.

Step B: Preparation of (S)-N'-[3-(3,4-dimethoxyphenylethylamino)-2-hydroxypropyl]-2-(4-methoxyphenyl)-4-methyl-6-pyrimidone hydrochloride, sesquihydrate Under $N_2$, NaH (722 mg, 0.018 mol) was added to a solution of product from Step A (3.5 g, 0.016 mol) in DMSO (150 ml) and the mixture was stirred at 60° C. for 0.5 hours. A solution of (S)-3-(3,4-dimethoxyphenylethyl)-5-(hydroxymethyl)oxazolid-2-one mesylate, (5.8 g, 0.016) in DMSO (150 ml) was added dropwise. After the addition the solution was stirred at 60° C. overnight. The reaction mixture was then cooled in an ice bath, poured into water, and extracted with $CH_2Cl_2$. The combined organic layers were washed with water, dried ($Na_2SO_4$), filtered and evaporated to dryness. The residue was refluxed with absolute ethanol (180 ml) and 10% NaOH (180 ml) for 2 hours, cooled to room temperature, poured into $H_2O$, and extracted with $CHCl_3$. The combined organic layers were washed with water and saturated NaCl solution, dried ($Na_2SO_4$), filtered, and evaporated to dryness. The residue was stirred with 6N ethanolic HCl solution (12 ml) to yield the hydrochloride salt which was recrystallized from 2-propanol giving 3.70 g (45%) of product which analyzed correctly for $C_{25}H_{31}N_3O_5 \cdot HCl \cdot 1\frac{1}{2}H_2O$. Structure was confirmed by 360 MHz 'HNMR and $^{13}C$ spectroscopy.

Using 2,4,5-trimethylpyrimidine-6-one; 4-methyl-2-phenylpyrimidine-6-one; 2-methyl-4-phenylpyrimidine-6-one and 2,4-diiphenylpyrimidine-6-one in place of 4-methyl-2-(p-methoxyphenyl)pyrimidine-6-one as described in Example 2 yielded (S)-N'-[3-(3,4-dimethoxyphenylethyl)amino-2-hydroxypropyl]-2,4,5-trimethylpyrimidine-6-one; (S)-N'-[3-(3,4-dimethoxyphenylethyl)amino-2-hydroxypropyl]-4-methyl-2-phenylpyrimidine-6-one; (S)-N'-[3-(3,4-dimethoxyphenylethyl)-amino-2-hydroxypropyl]-2-methyl-6-phenylpyrimidine-6-one and (S)-N'-[3-(3,4-dimethoxyphenylethyl)amino-2-hydroxypropyl]-2,4-diphenylpyrimidine-6-one, respectively.

EXAMPLE 3

(S)-N'-(3-isopropylamino-2-hydroxypropyl)-2-(4-methoxyphenyl)-4-methyl-6-pyrimidone hyrochloride.hemihydrate Under $N_2$, NaH (722 mg, 0.018 mol) was added to a solution of 6-hydroxy-4-methyl-2-(p-methoxyphenyl)-pyrimidine (3.5 g, 0.016 mol) in DMSO (150 ml) and the mixture was stirred at 60° C. for 0.5 hour. A solution of (S)-3-(2-propyl)-5-hydroxymethyloxazolid-2-one mesylate (3.95 g, 0.016 mol) in DMSO (150 ml) was added dropwise and the mixture was stirred at 60° C. overnight. The reaction mixture was then cooled to room temperature, poured into water, and extracted with $CHCl_3$. The combined organic layers were washed with water and saturated NaCl solution, dried ($Na_2SO_4$), filtered, and evaporated to dryness. The residue was heated at reflux with absolute ethanol (180 ml) and 10% NaOH (180 ml) for 2 hours cooled to room temperature, poured into $H_2O$, and extracted with $CHCl_3$. The combined organic layers were washed with $H_2O$ and saturated NaCl solution, dried ($Na_2SO_4$), and evaporated to dryness. The residue was chromatographed on silica gel with 5% $CH_3OH$—$CHCl_3$ as eluant. The resultant free base was converted to the hydrochloride salt by treatment with 6N HCl-ethanol solution (2.1 ml). The salt was recrystallized from 2-propanol yielding 780 mg (13%) of product which analyzed correctly for $C_{18}H_{25}N_3O_3 \cdot HCl \cdot \frac{1}{2}H_2O$. Structure was confirmed by 360 MHz HNMR and $^{13}C$ spectroscopy.

Using 4-methyl-2-phenylpyrimidine-6-one in place of 4-methyl-2-(p-methoxyphenyl)pyrimidine-6-one as described in Example 3 yielded (S)-N'-(3-isopropylamino-2-hydroxypropyl)-4-methyl-2-phenylpyrimidine-6-one.

EXAMPLE 4

(S)-5-chloro-6-[3-(3,4-dimethoxyphenylethylamino)-2-hydroxypropoxy]-2-(4-methoxyphenyl)-4-methylpyrimidine

Step A: Preparation of 5,6-dichloro-4-methyl-2-(p-methoxyphenyl)pyrimidine

A mixture of 5-chloro-6-hydroxy-2-(4-methoxyphenyl)-3-methylpyrimidine (1.0 g, 0.004 mol) and $POCl_3$ (8 ml) was heated at reflux under $N_2$ for 3 hours and then allowed to stand at 0° C. for 16 hours. Ice was added and the pH made basic with 10% NaOH. The solution was extracted with $CH_2Cl_2$. The combined organic layers were washed with water, dried ($Na_2SO_4$), filtered, and evaporated to dryness. The residue was recrystallized from ethylacetatehexane yielding 710 mg (66%) of product. The structure was confirmed by MS and 90 MHz 'HNMR.

Step B: Preparation of (S)-5-chloro-6-[3-(3,4-dimethoxyphenylethylamino)-2-hydroxypropoxy]-2-(4-methoxyphenyl)-4-methylpyrimidine p Under $N_2$, NaH (120 mg, 0.003 mol) was added to a solution of 3-(3,4-dimethoxyphenylethyl)-5-hydroxymethyl-2-phenyloxazolidine (1.03 g, 0.003 mol) in DMF (15 ml) and the mixture was stirred at 60° C. or 0.5 hours. The temperature was lowered to 25° C. and a solution of product from Step A (690 mg, 0.003 mol) in DMF (15 ml) was added. The solution was stirred at 60° C. overnight. The reaction mixture was cooled to room temperature and the DMF was removed under reduced pressure. The residue was partitioned between water and $CH_2Cl_2$. The basic aqueous layer was extracted with $CH_2Cl_2$. The combined organic layers were washed with water, dried ($Na_2SO_4$), filtered, and evaporated to dryness.

The residue was chromatographed on silica gel with 5% 2-propanol-$CH_2Cl_2$ as eluant and recrystallized from $CH_3CN$ twice to yield 50 mg (4%) of product; m.p. 94°–95° C. which analyzed correctly for $C_{25}H_{30}N_3O_5Cl$. The structure was confirmed by 360 MHz HNMR.

Using 2-methyl-4-phenylpyrimidine-6-one and 2,4-diphenylpyrimidine-6-one in place of 5-chloro-2-(p-methoxyphenyl)-4-methylpyrimidine-6-one as described in Example 4 yielded 5-chloro-2-methyl-4-phenylpyrimidine and 5-chloro-2,4-diphenylpyrimidine, respectively.

Using 5-chloro-2-methyl-4-phenylpyrimidine and 5-chloro-2,4-diphenylpyrimidine in place of 5,6-dichloro-4-methyl-2-(p-methoxyphenyl)pyrimidine as described in Example 4 yielded (S)-5-chloro-6-[3-(3,4-dimethoxyphenylethyl)amino-2-hydroxypropoxy]2-methyl-4-phenylpyrimidine and (S)-5-chloro-6-[3-(3,4-dimethoxyphenylethyl)amino-2-hydroxypropoxy]-2,4-diphenylpyrimidine.

Employing the procedures substantially as described in Examples 1, 2 or 3 with the appropriate starting materials there are produced the following compounds.
Employing the procedure of Example 4, with the appropriate starting materials provides the following compounds:
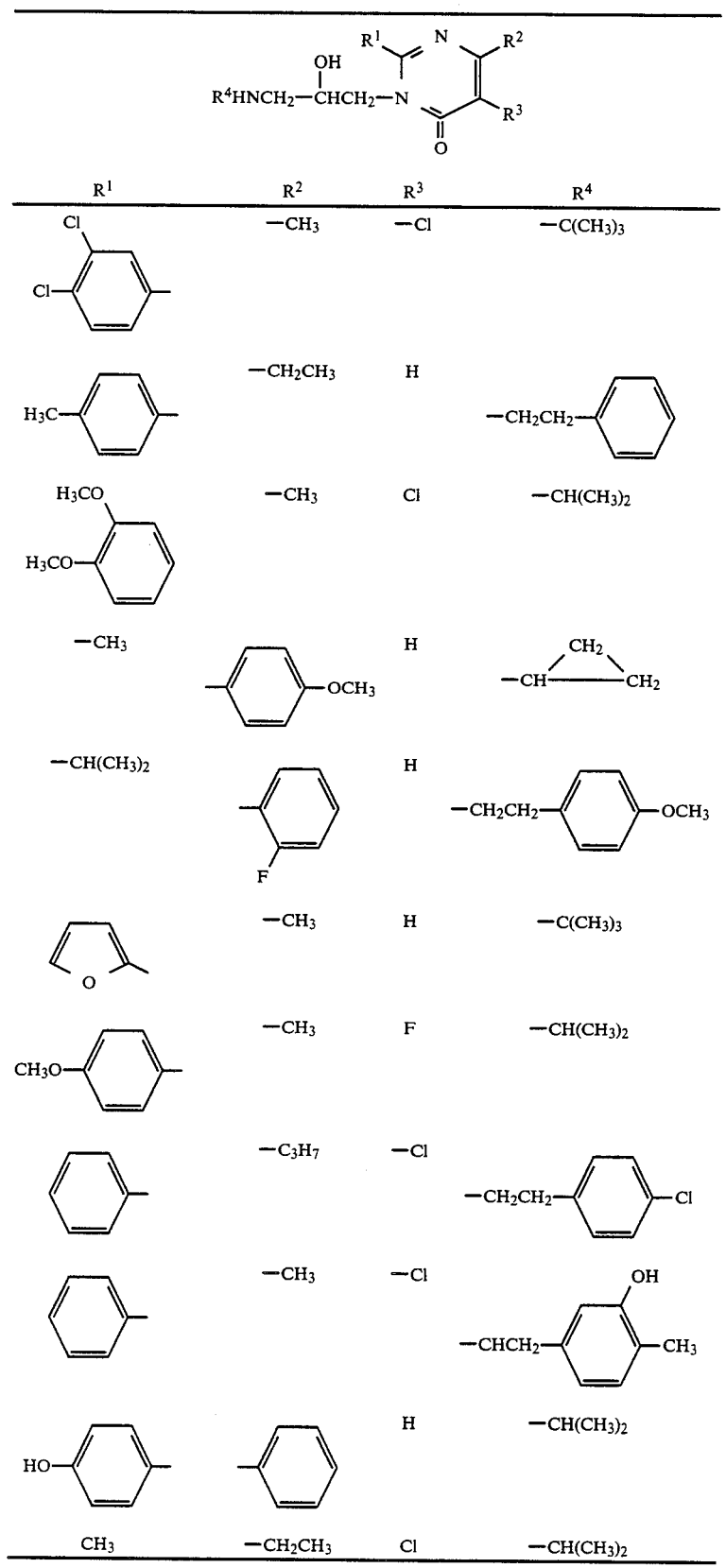

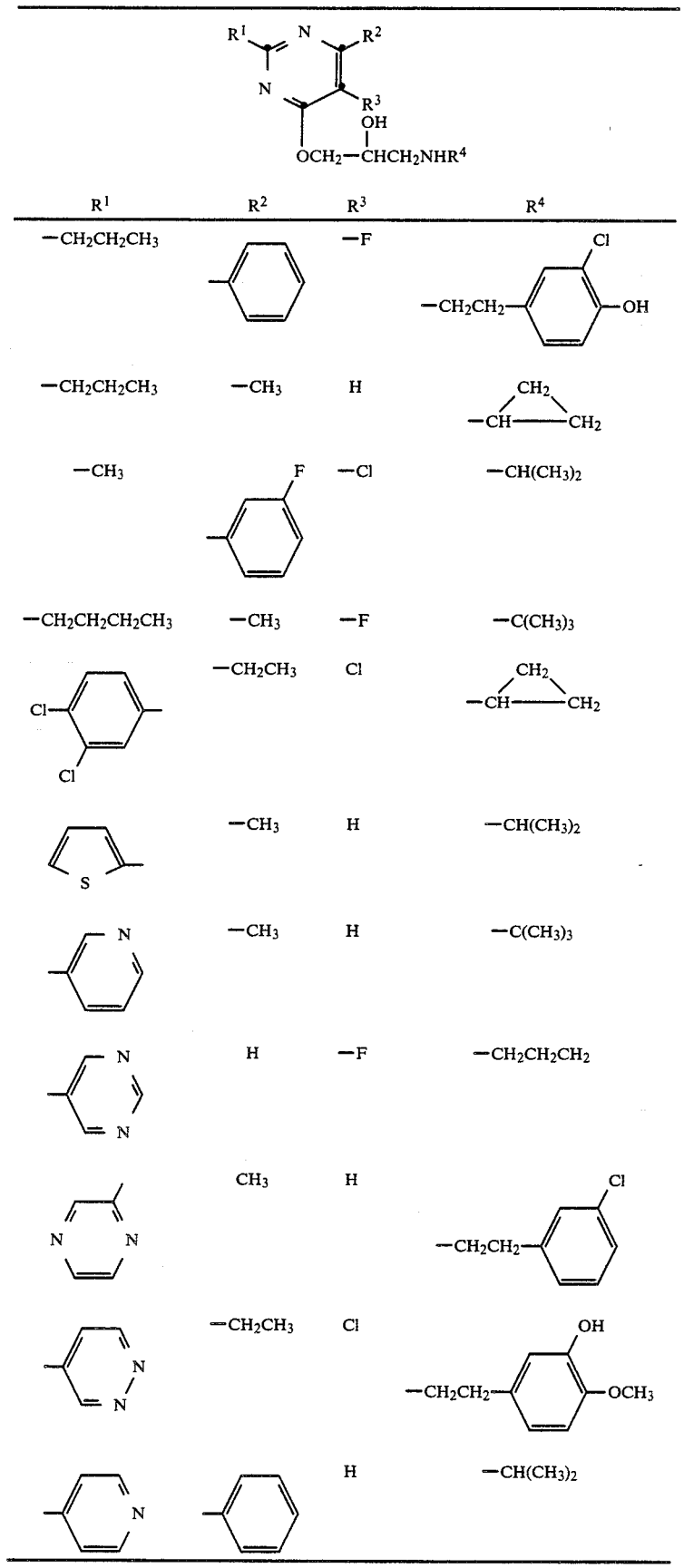

EXAMPLE 5

Tablet Formulation

| INGREDIENT | AMOUNT (Mg.) |
|---|---|
| (S)—5-Chloro-N'—{3,4-dimethoxyphenylethyl-amino)-2-hydroxypropyl}-2-(4-methoxyphenyl)-4-methyl-6-pyrimidone Hydrochloride | 40.0 |
| calcium phosphate | 120.0 |
| lactose | 50.0 |
| starch | 23.5 |
| magnesium stearate | 1.5 |

EXAMPLE 6

Capsule Formulation

| INGREDIENT | AMOUNT (Mg.) |
|---|---|
| (S)—N'—[3-(3,4-dimethoxyphenyl-ethylamino)-2-hydroxy-propyl]-2-(4-methoxyphenyl)-4-methyl-6-pyrimidone hydrochloride sesquihydrate | 250 |
| lactose, U.S.P. | 93 |
| talc | 7 |

EXAMPLE 7

Ocular Formulation

| INGREDIENT | AMOUNT (Mg) |
|---|---|
| (S)—N'—(3-isopropylamino-2-hydroxypropyl)-2-(4-methoxy-phenyl)-4-methyl-6-pyrimidone hydrochloride.hemihydrate | 15.0 |
| sodium phosphate monobasic .2H$_2$O | 6.10 |
| dibasic sodium phosphate .12H$_2$O | 16.80 |
| benzalkonium chloride | 0.10 |
| sodium hydroxide q.s. pH | 6.8 |
| water for injection q.s. ad. | 1.0 ml |

EXAMPLE 8

Liquid Suspension

| INGREDIENT | AMOUNT (Mg) |
|---|---|
| (S)—5-chloro-6-[3-(3,4-dimethoxyphenylethylamino)-2-hydroxypropoxy]-2-(4-methoxy-phenyl)-4-methylpyrimidine | 5.0 |
| Veegum H.V. | 3.0 |
| methyl parable | 1.0 |
| kaolin | 10.0 |
| glycerin | 250.0 |
| water, q.s. | 1 liter |

What is claimed is:

1. A compound of structural formula

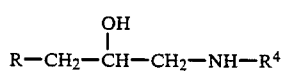

or a pharmaceutically acceptable salt thereof wherein:
R is

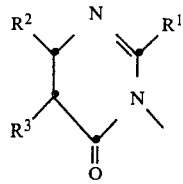

$R^1$ and $R^2$ are independently
(1) hydrogen,
(2) $C_{1-3}$alkyl, either straight or branched chain,
(3) phenyl or naphthyl either unsubstituted or substituted with 1 to 3 substituents selected from:
 (a) fluoro, chloro and bromo
 (b) $C_{1-3}$alkoxy, or
 (c) $C_{1-3}$alkyl;
(4) heterocyclic aryl of 5 or 6 members, at least 4 of which are carbon atoms and the hetero atoms are O, N or S selected from pyridinyl, pyrazinyl, pyrimidinyl, thienyl, furyl and N-methylpyrryl;

$R^3$ is
(1) hydrogen,
(2) halo,
(3) methyl; and $R^4$ is
(1) $C_{1-8}$alkyl, either straight or branched chain,
(2) $C_{3-6}$cycloalkyl,
(3) aryl-$C_{1-4}$alkyl, wherein the $C_{1-4}$alkyl moiety is straight or branched chain, and the aryl moiety is phenyl or naphthyl, either unsubstituted or substituted with 1 or 2 substituents selected from $C_{1-3}$alkyl, $C_{1-3}$alkoxy, hydroxy and halo.

2. The compound of claim 1, wherein:
$R^1$ is
(1) $C_{1-3}$alkyl, or
(2) phenyl
(3) 4-methoxyphenyl $R^2$ is
(1) $C_{1-3}$alkyl, or
(2) phenyl;

$R^3$ is
(1) hydrogen,
(2) methyl or
(3) halo; and $R^4$ is
(1) $C_{1-8}$alkyl,
(2) aryl-$C_{1-4}$alkyl, wherein the $C_{1-4}$alkyl moiety is ethyl and the aryl moiety is phenyl substituted with two $C_{1-3}$alkoxy groups, or
(3) $C_{3-6}$cycloalkyl.

3. The compound of claim 2, which is:
(S)-5-chloro-N'-[3-(3,4-dimethoxyphenylethylamino)-2-hydroxypropyl]-2-(4-methoxyphenyl)-4-methyl-6-pyrimidone;
(S)-N'-[3-(3,4-dimethoxyphenylethylamino)-2-hydroxypropyl]-2-(4-methoxyphenyl)-4-methyl-6-pyrimidone; or
(S)-N'-(3-isopropylamino-2-hydroxypropyl)-2-(4-methoxyphenyl)-4-methyl-6-pyrimidone;
or a pharmaceutically acceptable salt thereof.

4. A pharmaceutical β-blocker formulation comprising a pharmaceutically acceptable carrier and an effective amount of a β-blocker of structural formula:

$$R-CH_2-\underset{\underset{OH}{|}}{CH}-CH_2-NH-R^4$$

or a pharmaceutically acceptable salt thereof wherein;
R is

[structure with R², N, R¹, R³, N, =O]

R¹ and R² are independently
(1) hydrogen,
(2) $C_{1-3}$alkyl, either straight or branched chain,
(3) phenyl or naphthyl either unsubstituted or substituted with 1 to 3 substituents selected from:
   (a) halo, fluoro, chloro and bromo
   (b) $C_{1-3}$alkoxy,
   (c) $C_{1-3}$alkyl; or
(4) heterocyclic aryl of 5 or 6 members, at least 4 of which are carbon atoms and the hetero atoms are O, N or S selected from pyridinyl, pyrazinyl, pyrimidinyl, thienyl, furyl and N-methylpyrryl;

R³ is
(1) hydrogen,
(2) halo,
(3) methyl and

R⁴ is
(1) $C_{1-8}$alkyl, either straight or branched chain,
(2) $C_{3-6}$cycloalkyl,
(3) aryl-$C_{1-4}$alkyl, wherein the $C_{1-4}$alkyl moiety is straight or branched chain, and the aryl moiety is phenyl or naphthyl, either unsubstituted or substituted with 1 or 2 substituents selected from $C_{1-3}$alkyl, $C_{1-3}$alkoxy, hydroxy and halo.

5. The formulation of claim 4 wherein:
R¹ is
(1) $C_{1-3}$alkyl, or
(2) phenyl
(3) 4-methoxyphenyl R² is
(1) $C_{1-3}$alkyl, or
(2) phenyl.

6. The formulation of claim 5, wherein the β-blocker is:
(S)-5-chloro-N¹-[3-(3,4-dimethoxyphenylethylamino)-2-hydroxypropyl]-2-(4-methoxyphenyl)-4-methyl-6-pyrimidone;
(S)-N'-[3-(3,4-dimethoxyphenylethylamino)-2-hydroxypropyl]-2-(4-methoxyphenyl)-4-methyl-6-pyrimidone; or
(S)-N'-(3-isopropylamino-2-hydroxypropyl)-2-(4-methoxyphenyl)-4-methyl-6-pyrimidone; or
or a pharmaceutically acceptable salt thereof.

7. A method of producing an antihypertensive, cardioprotective, antiarrhythmic, and/or antianginal effect in a patient in need of such treatment which comprises the administration of an effective β-blocker amount of a compound of structural formula:

$$R-CH_2-\underset{\underset{OH}{|}}{CH}-CH_2-NH-R^4$$

or a pharmaceutically acceptable salt thereof wherein:
R is

[structure with R², N, R¹, R³, N, =O]

R¹ and R² are independently
(1) hydrogen,
(2) $C_{1-3}$alkyl, either straight or branched chain,
(3) phenyl or naphthyl either unsubstituted or substituted with 1 to 3 substituents selected from:
   (a) halo,
   (b) $C_{1-3}$alkoxy, or
   (c) $C_{1-3}$alkyl;
(4) heterocyclic aryl of 5 or 6 members, at least 4 of which are carbon atoms and the hetero atoms are O, N or S selected from pyridinyl, pyrazinyl, pyrimidinyl, thienyl, furyl and N-methylpyrryl;

R³ is
(1) hydrogen,
(2) halo, fluoro, chloro, and bromo
(3) methyl; and

R⁴ is
(1) $C_{1-8}$alkyl, either straight or branched chain,
(2) $C_{3-6}$cycloalkyl,
(3) aryl-$C_{1-4}$alkyl, wherein the $C_{1-4}$alkyl moiety is straight or branched chain, and the aryl moiety is phenyl or naphthyl, either unsubstituted or substituted with 1 or 2 substituents selected from $C_{1-3}$alkyl, $C_{1-3}$alkoxy, hydroxy and halo.

8. The method of claim 7 wherein:
R¹ is
(1) $C_{1-3}$alkyl, or
(2) phenyl
(3) 4-methoxyphenyl R² is
(1) $C_{1-3}$alkyl, or
(2) phenyl;

R³ is
(1) hydrogen,
(2) methyl, or
(3) halo; and

R⁴ is
(1) $C_{1-8}$alkyl,
(2) aryl-$C_{1-4}$alkyl, wherein the $C_{1-4}$alkyl moiety is ethyl and the aryl moiety is phenyl substituted with two $C_{1-3}$alkoxy groups or
(3) $C_{3-6}$cycloalkyl.

9. The method of claim 7, wherein the compound is:
(S)-5-chloro-N'-[3-(3,4-dimethoxyphenylethylamino)-2-hydroxypropyl]-2-(4-methoxyphenyl)-4-methyl-6-pyrimidone;
(S)-N'-[3-(3,4-dimethoxyphenylethylamino)-2-hydroxypropyl]-2-(4-methoxyphenyl)-4-methyl-6-pyrimidone; or
(S)-N'-(3-isopropylamino-2-hydroxypropyl)-2-(4-methoxyphenyl)-4-methyl-6-pyrimidone;
or a pharmaceutically acceptable salt thereof.

* * * * *